US010655107B2

(12) United States Patent
Ejiri et al.

(10) Patent No.: US 10,655,107 B2
(45) Date of Patent: May 19, 2020

(54) ADHERENT CELL CULTURE METHOD (71) Applicant: Corning Incorporated, Corning, NY (US)

(72) Inventors: Yoko Ejiri, Tsukuba (JP); Satoru Ayano, Tsukuba (JP); Masaya Hosoda, Tsukuba (JP); Go Tazaki, Tsukuba (JP)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/346,121

(22) PCT Filed: Sep. 20, 2012

(86) PCT No.: PCT/JP2012/005965
§ 371 (c)(1),
(2) Date: Mar. 20, 2014

(87) PCT Pub. No.: WO2013/042360
PCT Pub. Date: Mar. 28, 2013

(65) Prior Publication Data
US 2014/0227784 A1  Aug. 14, 2014

(30) Foreign Application Priority Data
Sep. 20, 2011  (JP) ................ 2011-204796

(51) Int. Cl.
*C12N 5/09* (2010.01)
*C12M 1/00* (2006.01)
*C12M 1/32* (2006.01)

(52) U.S. Cl.
CPC ........... *C12N 5/0693* (2013.01); *C12M 23/12* (2013.01); *C12M 23/20* (2013.01)

(58) Field of Classification Search
None
See application file for complete search history.

(56) References Cited

U.S. PATENT DOCUMENTS

| | | | |
|---|---|---|---|
| 5,792,653 A | 8/1998 | Weibezahn et al. | |
| 9,670,462 B2 | 6/2017 | Du et al. | |
| 2005/0101010 A1 | 5/2005 | Pakhung | |
| 2009/0075366 A1 | 3/2009 | Tazaki et al. | |
| 2010/0068793 A1* | 3/2010 | Ungrin ................. | B01L 3/5085 435/283.1 |
| 2011/0217725 A1* | 9/2011 | Itchoda ................. | C12M 23/12 435/29 |
| 2011/0233656 A1 | 9/2011 | Ohta et al. | |

FOREIGN PATENT DOCUMENTS

| | | | |
|---|---|---|---|
| EP | 2 343 361 A1 | 7/2011 | |
| JP | 1-234795 A | 9/1989 | |
| JP | 06-327462 | 11/1994 | |
| JP | 8-99477 A | 4/1996 | |
| JP | 2716646 | 2/1998 | |
| JP | 2000 126606 | 5/2000 | |
| JP | 2002 335949 | 11/2002 | |
| JP | 2004-51 A | 1/2004 | |
| JP | 2005-27598 A | 2/2005 | |
| JP | 2008 022743 | 2/2008 | |
| JP | 2008220205 A | 9/2008 | |
| JP | 2009022276 A | 2/2009 | |
| JP | 2009-50194 A | 3/2009 | |
| JP | 2009-82005 A | 4/2009 | |
| JP | 2010022366 A | 2/2010 | |
| JP | 2010 88347 | 4/2010 | |
| JP | WO 2010047132 A1 * | 4/2010 | ............ C12M 23/12 |
| JP | 2010148386 A | 7/2010 | |
| JP | 2010233456 A | 10/2010 | |
| KR | 2006-0117945 A | 11/2006 | |
| KR | 10-2011-0074773 A | 7/2011 | |
| WO | 2007097121 A1 | 8/2007 | |
| WO | WO 2011/083768 A1 | 7/2011 | |
| WO | 2011098402 A1 | 8/2011 | |

OTHER PUBLICATIONS

Yoshimoto et al. "Inverted pattern formation of cell microarrays on poly (ethylene glycol)(PEG) gel patterned surface and construction of hepatocyte spheroids on unmodified PEG gel microdomains", Lab Chip 9 (9): 1286-1289, 2009.*
Cole et al. "Stimuli-responsive interfaces and systems for the control of protein-surface and cell-surface interactions", Biomaterials 30(9): 1827-1850, 2009.*
Khademhosseini et al. "Micromolding of photocrosslinkable hyaluronic acid for cell encapsulation and entrapment", Journal of Biomedical Materials Research Part A 79 (3): 522-532, 2006.*
Cheng et al. "Surface chemical patterning for long-term single-cell culture", Journal of Biomedical Materials Research A 96A(3): 507-512, 2011.*
Your Dictionary "cylinder", available online at <<http://www.yourdictionary.com/cylinder>>, Webster's New World College Dictionary, Fifth Edition, Houghton Mifflin Harcourt Publishing Company, copyright 2014 (Year: 2014).*
Nakamura et al. "Evaluation of drug toxicity with hepatocytes cultured in a micro-spacecell culture system." Journal of Bioscience and Bioengineering 111.1 (2011): 78-84 (Year: 2011).*

(Continued)

*Primary Examiner* — Emily A Cordas
(74) *Attorney, Agent, or Firm* — Annie J. Kock; Therese M. Finan (57) ABSTRACT

Provided are a method capable of evaluating adherent cells under an environment similar to an in vivo environment by a culture method similar to a two-dimensional culture, and applications thereof. An adherent cell culture method uses, as a culture chamber (10), a chamber in which two or more culture spaces each having an equivalent diameter (D) that is 1 to 5 times the diameter of a desired spheroid and each having a height (H) that is 0.3 to 5 times the equivalent diameter are arranged and a surface of each of the culture spaces has a water contact angle of 45 degrees or less. Spheroids of adherent cells are cultured in the respective culture spaces (11) arranged in the culture chamber (10).

18 Claims, 8 Drawing Sheets

(56) References Cited

OTHER PUBLICATIONS

Friedrich, J. et al., "Spheroid-based drug screen: considerations and practical approach", Nature Protocols, vol. 4, No. 3 pp. 309-324, (2009).
Ikada, Y., "Surface modification of polymers for medical applications", Biomaterials 1994, vol. 15, No. 10, pp. 725-736 (1994).
International Search Report dated Dec. 18, 2012 in PCT/JP12/005965 Filed Sep. 20, 2012.
Office Action dated Oct. 16, 2015 in Korean Patent Application No. 10-2014-7009797 (with partial English translation).
Office Action dated Aug. 11, 2016 in Korean Patent Application No. 10-2014-7009797 (with partial English translation).
Office Action dated Jul. 5, 2016 in corresponding Japanese Patent Application No. 2013-534598, with English translation, 6 pp.
Office Action dated May 20, 2016 in corresponding Canadian Patent Application No. 2,848,875, 3 pages.
Japanese Office Action dated Feb. 14, 2017 in Patent Application No. 2013-534598 (with partial English translation).
Machine Translation of CN201280045911.5 Office Action dated Oct. 21, 2014; 5 Pages; Chinese Patent Office.
Machine Translation of JP2013534598 Notice of Allowance dated Mar. 18, 2018; 2 Pages; Japanese Patent Office.
Machine Translation of KR1020177014232 Office Action dated Dec. 28, 2018; 4 Pages; Korean Patent Office.
Supplementary European Search Report for EP12833898; dated Mar. 27, 2015; 2 Pages; European Patent Office.

\* cited by examiner

ADHERENT CELL CULTURE METHOD

CROSS REFERENCE TO RELATED APPLICATIONS

The present application is a 35 U.S.C. § 371 national stage patent application of International patent application PCT/JP2012/005965, filed on Sep. 20, 2012, published as WO/2013/042360 on Mar. 28, 2013, the text of which is incorporated by reference, and claims the benefit of the filing date of Japanese application no. 2011-204796, filed on Sep. 20, 2011, the text of which is also incorporated by reference.

TECHNICAL FIELD

The present invention relates to a method for culturing spheroids of adherent cells of a uniform size, which has never been achieved in a conventional two-dimensional culture (culture on a flat surface), by an operation similar to that of the two-dimensional culture.

BACKGROUND ART

In recent years, cells cultured by cell culture techniques have been used for drug efficacy tests and drug toxicity tests. However, cells cultured by the conventional culture techniques extend two-dimensionally and have a shape that is significantly different from that in vivo. This poses a problem that the cells do not have their original cell functions, which makes it difficult to reflect the behavior of drugs in vivo.

Under such circumstances, a spheroid culture method for simulating the morphology of tissues in vivo has attracted attention in recent years. For example, a method is disclosed in which the bottom surface of a 96-multiwell plate is formed into a funnel shape and a single spheroid is formed therein (Patent Literature 1). Other examples of the spheroid culture method include a technique in which a fine honeycomb structure is formed in a culture bottom surface to reduce the adhesion properties of cells with respect to material, thereby forming spheroids (Patent Literature 2), and a method using an exogenous cell aggregation agent (Patent Literature 3).

CITATION LIST

Patent Literature

[Patent Literature 1] Japanese Patent No. 2716646
[Patent Literature 2] Japanese Unexamined Patent Application Publication No. 2002-335949
[Patent Literature 3] Japanese Unexamined Patent Application Publication No. 2008-22743

SUMMARY OF INVENTION

Technical Problem

However, in the culture method disclosed in Patent Literature 1, a single spheroid is formed in a floating state within a single chamber. In this method, cells are liable to be detached from the chamber upon replacement of a culture medium, which poses a problem that the operation upon replacement of the culture medium becomes troublesome. In addition, since a single spheroid is formed within a single chamber, it is difficult to apply the culture method to, for example, a 6-well, 12-well, 24-well, or 384-well plate, or a flask-shaped chamber.

The culture methods disclosed in Patent Literature 2 and 3 can be applied to the above-mentioned culture plates and flask-shaped chamber, but cannot control the size of each spheroid. This poses a problem that it is difficult to form spheroids having a uniform diameter.

Thus, there are limitations to applying conventional culture methods to the commercially-available well plates and flask-shaped chamber. Even if the methods can be applied to the well plates and flask-shaped chamber, the methods cannot control the diameter of each spheroid. Accordingly, there is a demand for a new method that can be applied to various shapes of culture chambers and is capable of culturing spheroids of adherent cells having a uniform diameter by controlling the size of each spheroid.

Solution to Problem

In one aspect of an adherent cell culture method according to the present invention, a chamber is selected, as a culture chamber, in which two or more culture spaces each having an equivalent diameter that is 1 to 5 times the diameter of a desired spheroid and each having a height that is 0.3 to 5 times the equivalent diameter are arranged and a surface of each of the culture spaces has a water contact angle of 45 degrees or less. Spheroids of adherent cells are cultured in the respective culture spaces arranged in the selected culture chamber. The size of spheroids to be cultured is controlled by using the culture chamber in which the culture spaces are formed depending on the size of spheroids to be cultured. Consequently, spheroids of a desired size can be obtained.

In one aspect of the adherent cell culture method according to the present invention, the culture spaces preferably have an equivalent diameter in a range of 100 μm to 5000 μm. In addition, a wall partitioning the adjacent culture spaces preferably has a thickness in a range of 5 μm to 50 μm, and an angle formed between an upper surface and a side surface of the wall partitioning the adjacent culture spaces is preferably in a range of 90 degrees to 135 degrees.

Further, 60% or more of all cultured spheroids preferably have a diameter within a range of ±5% of an average value of diameters of the spheroids obtained after the culture. The spheroids are preferably cancer cells.

Furthermore, the culture chamber is preferably formed of a resin molded product that is made of one selected from the group consisting of acrylic resin, polylactic acid, polyglycolic acid, styrene resin, acrylic-styrene copolymer resin, polycarbonate resin, polyester resin, polyvinyl alcohol resin, ethylene-vinylalcohol copolymer resin, thermoplastic elastomer, vinyl chloride resin, and silicon resin, or a combination thereof.

In addition, the surface of each of the culture spaces is preferably processed by glass processing or by forming a functional group thereon by plasma treatment so that the surface has a water contact angle of 45 degrees or less.

Moreover, the surface of each of the culture spaces is preferably processed by one of the following methods: coating a polymer having hydrophilic and hydrophobic properties that vary depending on temperature or light; immobilizing a hydrophilic polymer chain that inhibits cell adhesion; and immobilizing a phospholipid or a phospholipid-polymer complex.

Advantageous Effects of Invention

According to the present invention, spheroids of adherent cells of a uniform size can be cultured at a high density by an operation similar to that of the conventional two-dimensional culture.

DESCRIPTION OF EMBODIMENTS

Hereinafter, an embodiment of the present invention will be described with reference to the drawings. However, the present invention is not limited to the embodiment described below. For clarity of explanation, omissions and simplification are made as appropriate in the following description and the drawings. The components having the same structure or function and corresponding parts in the drawings are denoted by the same reference numerals, and the description thereof is omitted.

Figure 1:
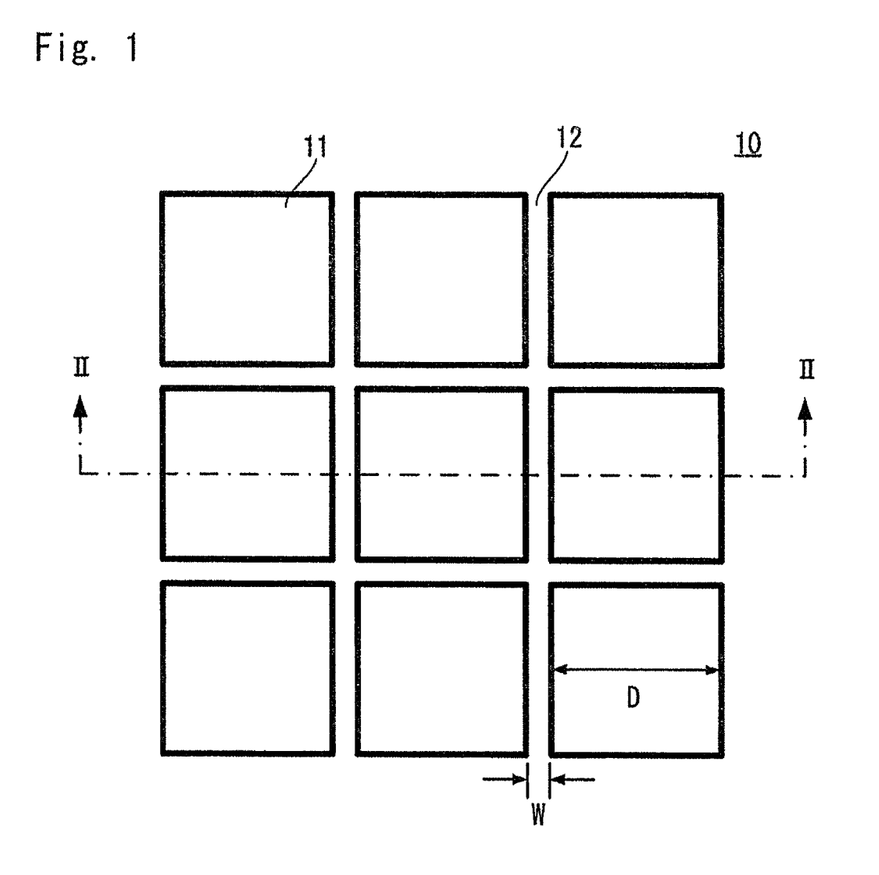
FIG. 1 is a diagram showing a structural example of a culture chamber according to an embodiment of the present invention.
Figure 2:
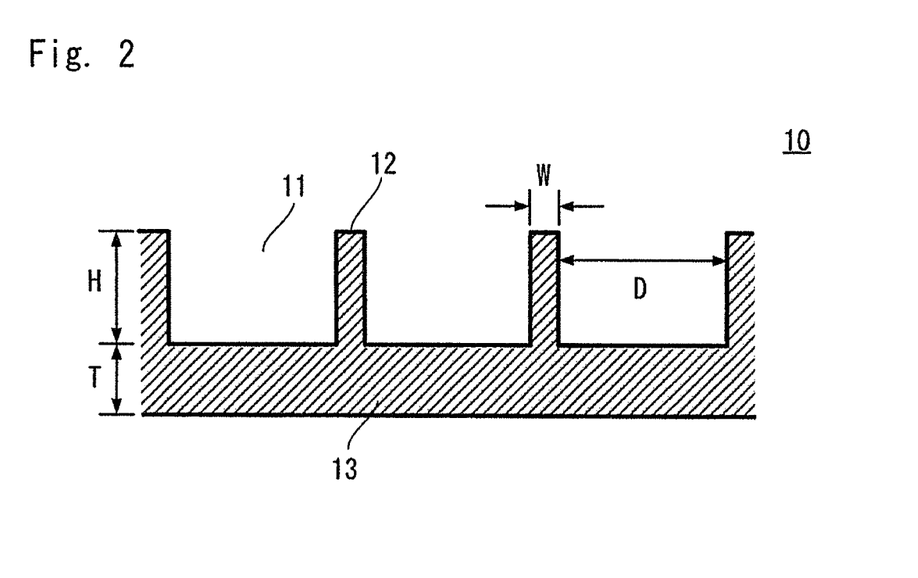
FIG. 2 is a sectional view taken along the line II-II of the culture chamber shown in FIG. 1.

FIG. 1 shows a structural example of a culture chamber according to an embodiment of the present invention. FIG. 2 shows a sectional view taken along the line II-II of FIG. 1.

A culture chamber 10 includes culture spaces 11, walls 12, and a bottom portion 13.

Each culture space 11 is a region partitioned by the walls 12 and the bottom portion 13, and serves as a three-dimensional space region (culture region) in which cells are cultured. Each culture space 11 is also referred to simply as a "space" or "micro-space".

Each wall 12 is a partition wall that partitions the culture spaces 11, and is also referred to as a convex portion that forms a concave-convex pattern in the culture chamber 10.

The bottom portion 13 functions as a substrate of the culture chamber 10, and the surface on which the culture spaces 11 are disposed serves as a part of the culture region (culture surface).

As for the culture spaces 11 in the culture chamber 10, FIGS. 1 and 2 show an equivalent diameter D, a height H, a width W (thickness) of each wall 12, and a thickness T of the bottom portion 13. FIGS. 1 and 2 show a case where the bottom portion 13 is integrally formed with the walls 12.

The term "equivalent diameter D" refers to the diameter of an inscribed circle inscribed in each culture space 11. More specifically, the term "equivalent diameter D" refers to the diameter of an inscribed circle inscribed in the shape of the surface (front surface shape) parallel to the bottom portion 13 of each culture space 11, i.e., the shape of the surface perpendicular to the direction of the height H of each culture space 11. When the shape of the front surface of each culture space 11 varies depending on the height H, a maximum equivalent diameter of the space region in which adherent cells are cultured is defined as the equivalent diameter.

The term "height H" refers to the length between the bottom of each culture space 11 and the upper surface of each wall 12, and also refers to the depth of each culture space 11. When the culture bottom surface is a flat surface, the height H is equal to the height of each wall 12. The term "width W" of each wall 12 also refers to a distance between the adjacent culture spaces 11.

The present inventors have found that spheroids of adherent cells having a uniform diameter can be cultured by using the culture chamber 10 which includes a plurality of culture spaces 11 each having the equivalent diameter D that is 1 to 5 times the diameter of a desired spheroid and each having the height H (depth) that is 0.3 to 5 times the equivalent diameter D and in which the surface of each culture space has a water contact angle of 45 degrees or less, and by culturing adherent cells in the respective culture spaces 11. Accordingly, the size of spheroids to be cultured can be controlled by selecting the size of the culture spaces 11, which are disposed in the culture chamber 10, depending on the size of a desired spheroid.

Figure 3:
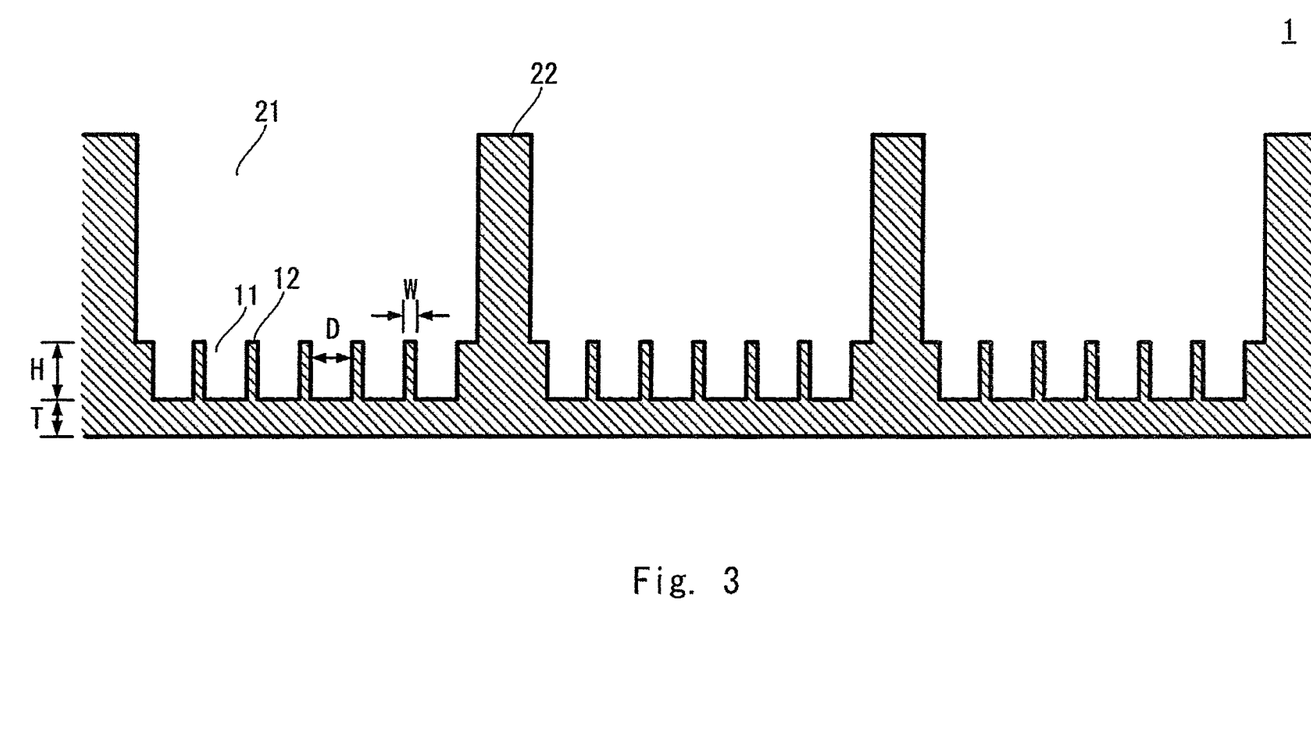
FIG. 3 is a schematic view for explaining a structural example in which a culture chamber according to an embodiment of the present invention is formed in each well of a culture plate.

FIG. 3 is a schematic view for explaining a structural example in which the culture chamber according to this embodiment is formed in each well of a culture plate. A culture plate 1 has a plurality of wells 21 formed therein, and the adjacent wells 21 are partitioned by partitions 22. Each well 21 corresponds to the culture chamber 10, and includes a plurality of culture spaces 11 and walls 12.

In each well 21, i.e., in each culture chamber 10, the plurality of culture spaces 11 are arranged in an array as shown in FIG. 1. The number of the culture spaces 11 included in each well 21 depends on the number of the wells 21 (the size of the wells 21) formed in the culture plate and the size of each of the culture spaces 11 and walls 12. In FIG. 3, which is a schematic view shown for explaining the above structure, the number of the culture spaces 11 is reduced, and the number of the culture spaces 11 included in each well 21 is different from the actual number of the culture spaces. In addition, FIGS. 1 and 2 show nine culture spaces 11. These are illustrated for explanation, and the number of the culture spaces 11 does not correspond to the actual number of the culture spaces 11 included in each culture chamber 10 (well 21).

Referring to FIGS. 1 to 3, examples of the shape and size of the micro-order culture spaces 11 for forming a desired spheroid, a hydrophilic treatment method for a culture surface, and a culture method will be described in detail.

As for the equivalent diameter of each culture space 11, it is necessary to take into consideration that the diameter of each spheroid increases as the cells proliferate. In this regard, it is important to secure the culture spaces 11 having such a structure that the spheroids in the adjacent culture spaces 11 are prevented from coming into contact with each other. Accordingly, the equivalent diameter D of each culture space 11 is preferably in the range of 1 to 5 times the diameter of a desired spheroid, and more preferably in the range of 1.5 to 3 times the diameter of a desired spheroid.

In one aspect of the culture method of the present invention, the culture chamber 10 having the following structure is used to form spheroids of adherent cells having a diameter of 100 μm. That is, the culture chamber 10 includes the bottom portion 13 on which the culture spaces 11, each of which has the equivalent diameter D that is 1 to 5 times the diameter of a desired spheroid, i.e., the equivalent diameter D ranging from 100 to 500 μm, and the height H that is 0.3 to 5 times the equivalent diameter, are regularly arranged.

For example, consider the case of culturing cancer cells which are adherent cells. According to Non Patent Literature 1 (Juergen Friedrich et al., "Spheroid-based drug screen: considerations and practical approach", Nature Protocols vol. 4 No. 3 2009, pp. 309-324), in the case where adherent cells are used for drug screening, spheroids of cancer cells which have proliferated have a minimum size of 200 μm, and the maximum size thereof varies depending on the organ from which the cells are derived, and is, for example, 1000 μm or greater. In addition, a phenomenon similar to secondary cell death occurring at the center of a tumor, which is a characteristic of tumors in vivo, is observed in spheroids ranging from 500 μm to 600 μm. In view of the above, the equivalent diameter of each of the culture spaces 11 is preferably in the range of 200 μm to 4000 μm, and more preferably in the range of 500 μm to 3000 μm.

As for the height H of each of the culture spaces 11, a space having a depth greater than that of a space for use in a typical culture method is used as each culture space 11 of the present invention. Specifically, in the typical culture method, adherent cells are allowed to proliferate and maintained by increasing the cell adhesion properties with respect to the surface of each culture space 11. In this culture method, unlike this embodiment, cells are not cultured in such deep spaces as the culture spaces 11 having the equivalent diameter D in the range of 1 to 5 times the diameter of a desired spheroid and having the height H in the range of 0.3 to 5 times the equivalent diameter D, in order to enhance amino acids and oxygen supply capabilities.

On the other hand, according to the present invention, the cell adhesion properties are suppressed as described below, so it is necessary to be able to supply amino acids, oxygen, and the like and to design the optimum height H so as to prevent spheroids from being detached from the culture spaces. As a result of studies on various heights H and equivalent diameters D of the culture spaces 11, it has been found that the optimum range of the height H of the culture spaces 11 is the range of 0.3 to 5 times the equivalent diameter D of the culture spaces 11, and more preferably, the range of 0.5 to 2 times the equivalent diameter D. One reason for this is that the height H of the culture spaces 11 may be set to a value that prevents spheroids from being detached from the culture spaces 11 upon replacement of a culture medium and moreover it is preferable to use spaces as shallow as possible so as to sufficiently supply amino acids, oxygen, and nutrient contained in the culture medium.

The width W of each wall 12 corresponds to the thickness of each wall 12 that partitions the adjacent culture spaces 11. Accordingly, in order to prevent proliferation of cells on the upper surface of each wall 12 and put cells into the culture spaces 11 easily, the width W of the wall 12 is preferably in the range of 5 to 50 μm, and is preferably equal to or smaller than the size of a single cell body, that is, preferably in the range of 5 to 30 μm, and more preferably, in the range of 5 to 10 μm. Further, for the same reasons, an angle θ formed between an upper surface of each wall 12 and a side surface of each culture space 11 is preferably in the range of 90 degrees to 135 degrees, and more preferably in the range of 90 degrees to 120 degrees.

Figure 4:
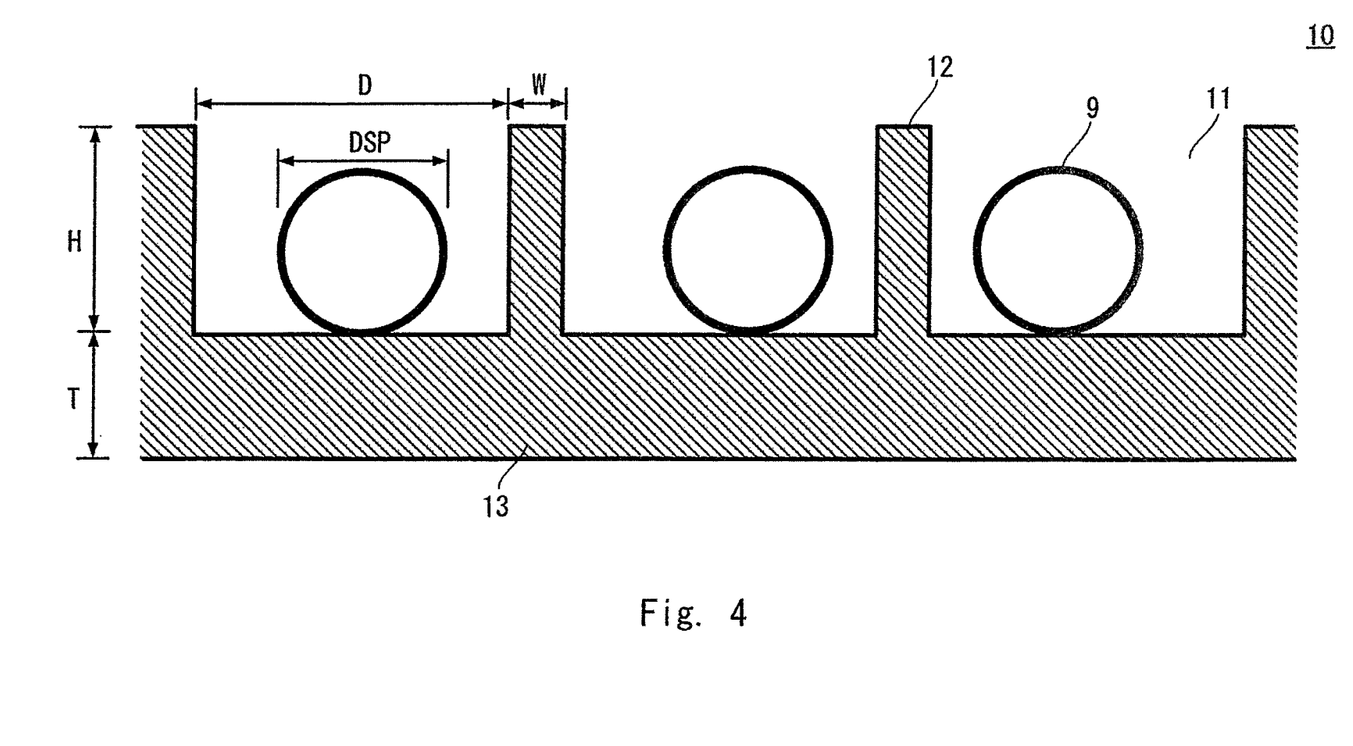
FIG. 4 is a schematic view showing a state in which a spheroid is cultured in each culture space.

FIG. 4 is a schematic view showing a state in which spheroids are cultured in the respectively culture spaces 11. In FIG. 4, the sectional view of FIG. 2 is used and each spheroid 9 is represented by the mark "○". The spheroids 9 are cultured in the respective culture spaces 11.

In the case of culturing cells in the culture plate 1 shown in FIG. 3, setting of culture conditions, replacement of a culture medium, and the like are carried out for each well 21. Accordingly, since the plurality of culture spaces 11 can be formed in each well 21, a plurality of spheroids can be cultured under the same conditions. In addition, since spheroids can be cultured using the well plate, a device and the like for use in the conventional cell culture can be used.

Assuming that a diameter DSP of each spheroid 9 has a value dsp (dsp is a positive value), the equivalent diameter D of each culture space 11 is in the range of 1 to 5 times the value dsp (dsp≤D≤5dsp). The height H of each culture space 11 is in the range of 0.3 to 25 (5×5) times the value dsp (0.3dsp≤H≤25dsp).

Figure 5A:
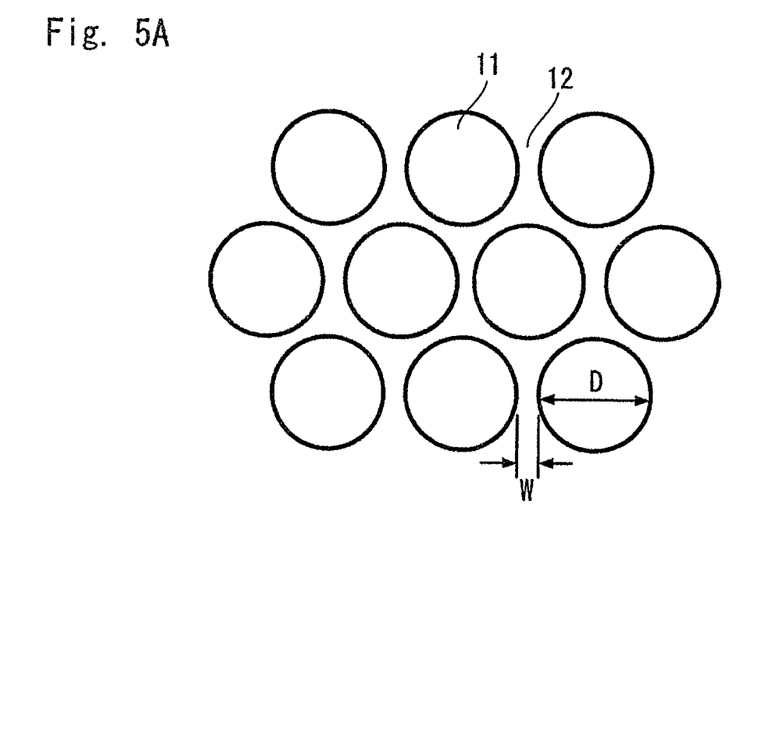
FIG. 5A is a diagram showing another example of the shape of each culture space.
Figure 5B:
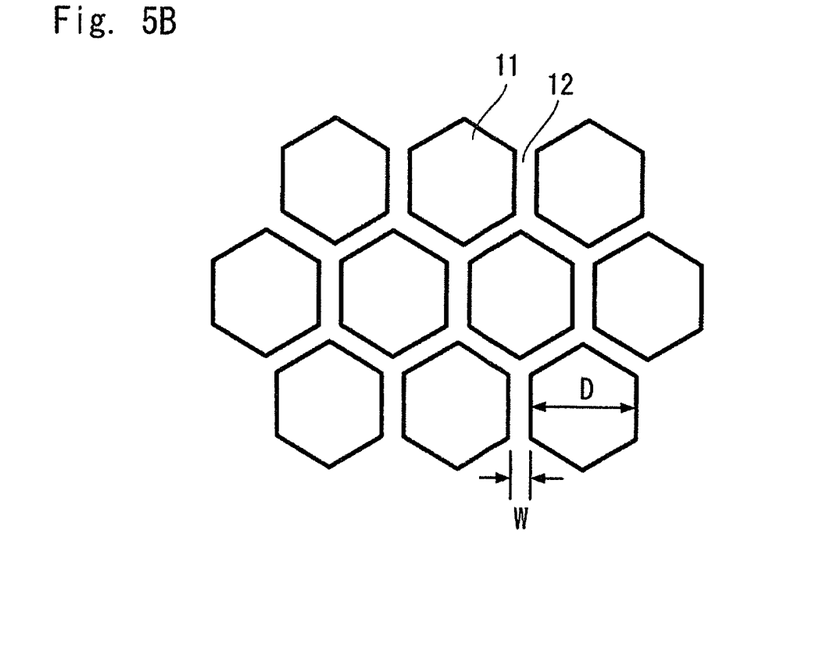
FIG. 5B is a diagram showing a still further example of the shape of each culture space.

The shape (front surface shape) of each culture space 11, or the shape of the surface parallel to the bottom portion 13, is not limited to the shape shown in FIG. 1. For example, the shapes shown in FIGS. 5A and 5B and other shapes (an ellipse, a rhomboid, etc.) can also be employed. A symmetrical structure is preferably employed so that spheroids having a uniform diameter can be formed at a high density.

Figure 6A:
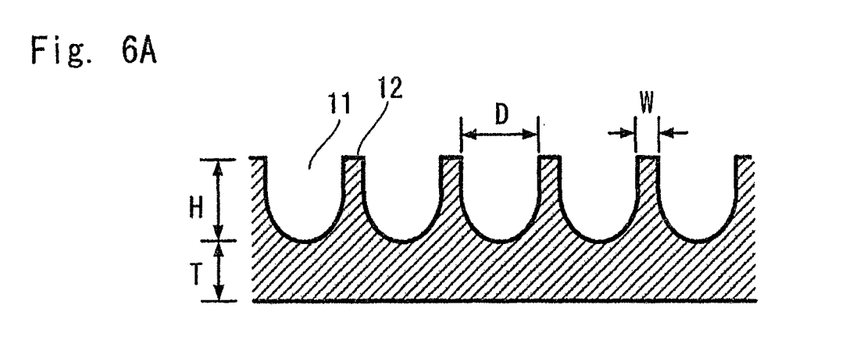
FIG. 6A is a sectional view showing an example of the shape of a side surface of each culture space.
Figure 6B:
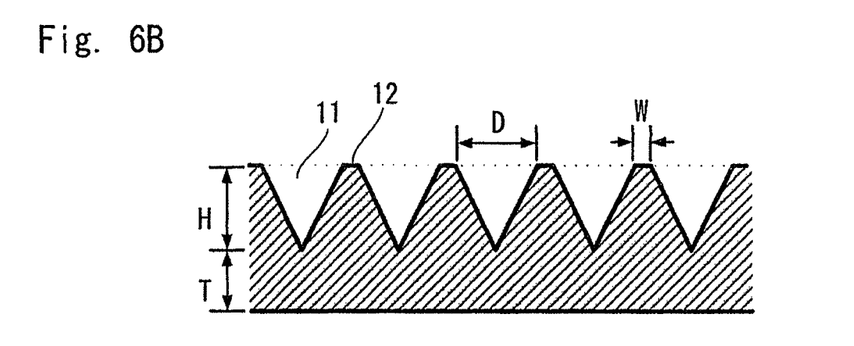
FIG. 6B is a sectional view showing a further example of the shape of the side surface of each culture space.
Figure 6C:
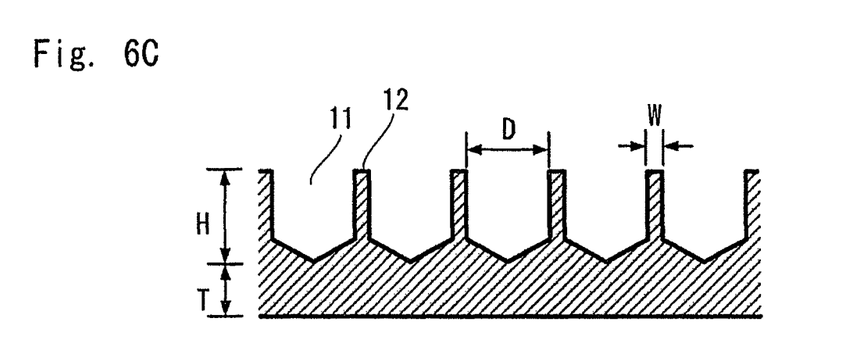
FIG. 6C is a sectional view showing a still further example of the shape of the side surface of each culture space.
Figure 7:
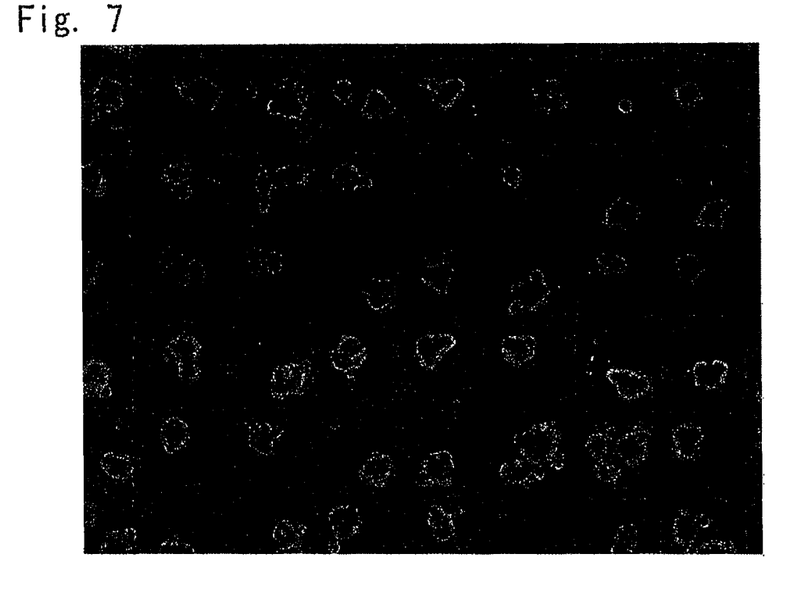
FIG. 7 is a photograph showing results of Example 1.
Figure 8:
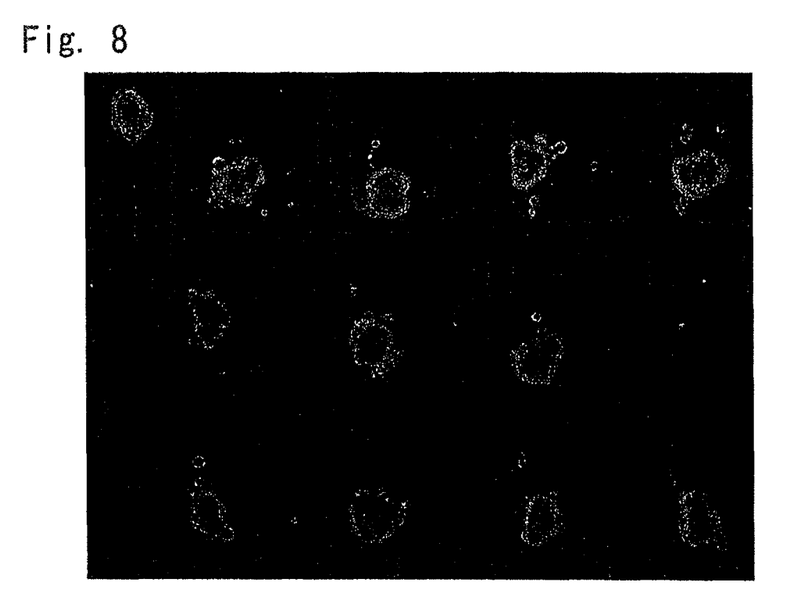
FIG. 8 is a photograph showing results of Example 2.
Figure 9:
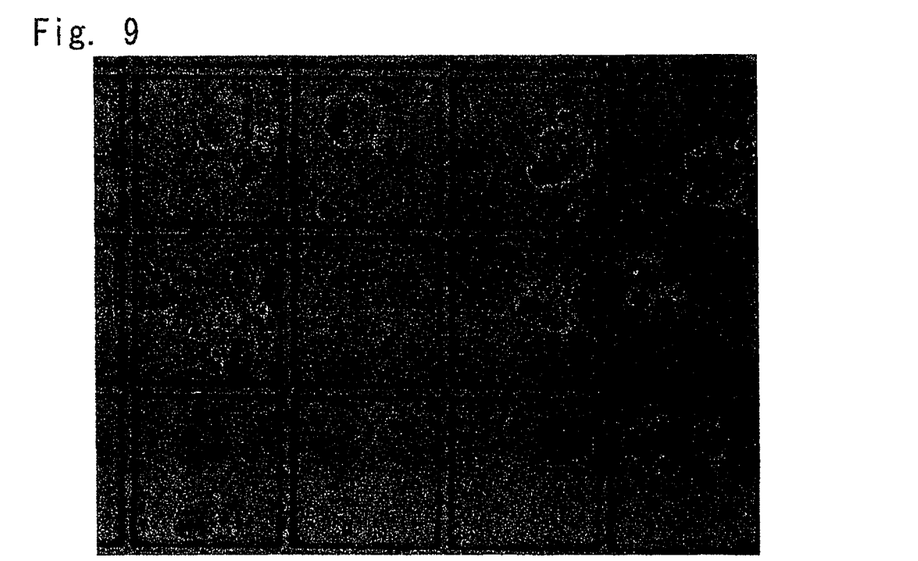
FIG. 9 is a photograph showing results of Comparative Example 1.
Figure 10:
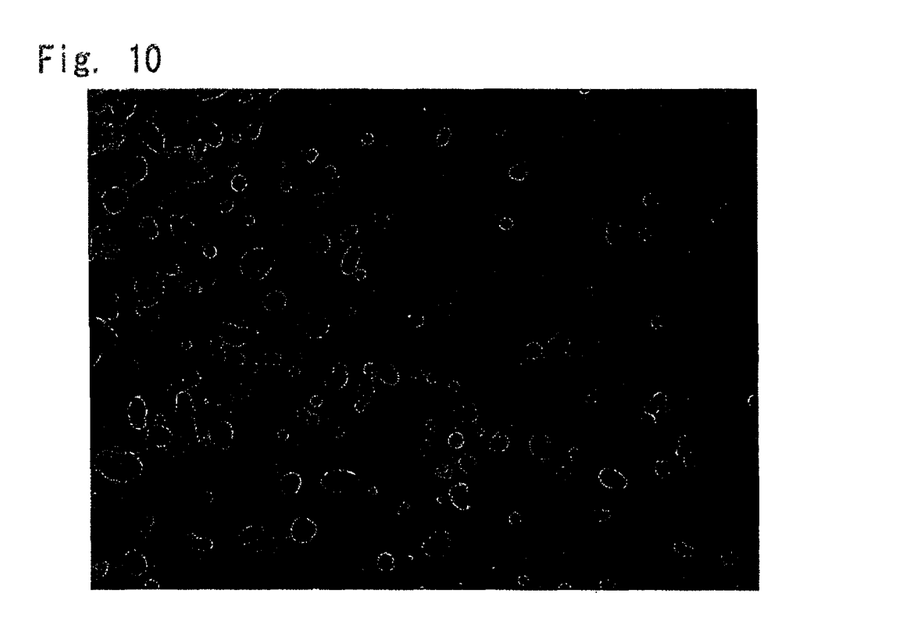
FIG. 10 is a photograph showing results of Comparative Example 2.

The shape of the side surface of each culture space 11 is not limited to the cylindrical shape shown in FIG. 2. For example, the shapes shown in FIGS. 6A to 6C can also be employed.

A material for forming the culture chamber 10 is selected from the group consisting of acrylic resin, polylactic acid, polyglycolic acid, styrene resin, acrylic-styrene copolymer resin, polycarbonate resin, polyester resin, polyvinyl alcohol resin, ethylene-vinylalcohol copolymer resin, thermoplastic elastomer, vinyl chloride resin, and silicon resin, or a combination thereof.

In terms of observation performance, the thickness T of the bottom portion 13 of the culture chamber 10 is preferably 1 mm or less. However, the thickness may be 1 mm or more, as long as the thickness has no adverse effect on the observation with a microscope, and thus the thickness T of the bottom portion 13 is not limited. By securing the observation performance of the bottom portion 13 of the culture chamber, the cultured spheroids can be observed by using the culture plate without any change.

Next, the characteristics of the culture surface will be described. A culture medium is injected into each culture space 11, and when a coating solution is used, the surface cannot be covered unless the solution is injected into each culture space 11. For this reason, the water contact angle of the culture surface is preferably 45 degrees or less, and is more preferably in the range of 0 to 20 degrees. The value of the water contact angle is determined based on values obtained by preparing and measuring a flat plate with no concave-convex pattern of the culture spaces 11 and the walls 12 under the same conditions as those for the culture chamber 10.

As for the surface in which the culture spaces 11 are arranged in an array, in the case where the surface has a high hydrophobic property and a water contact angle of more than 45 degrees, that is, the surface has low wettability, when a culture medium or coating solution is added, air bubbles are liable to be trapped in each space, which may result in generation of a space in which cells cannot be cultured. Accordingly, it is necessary to perform a hydrophilic treatment so that the water contact angle becomes 45 degrees or less. Examples of the hydrophilic treatment method include a method of depositing $SiO_2$ and a method of performing a plasma treatment.

In addition, it is preferable to suppress the cell adhesion properties so as to improve the rate of formation of spheroids. The cell adhesion properties can be suppressed by using the surface having a water contact angle of 45 degrees or less, preferably 40 degrees or less, and more preferably 20 degrees or less. The relationship between the suppression of cell adhesion properties and the water contact angle is disclosed in, for example, Non Patent Literature 1 (Y Ikada, "Surface modification of polymers for medical applications", Biomaterials 1994, vol. 15 No. 10, pp. 725-736).

Examples of a method for setting the water contact angle to 45 degrees or less include a method of depositing glass on the culture bottom surface, and a method of forming a function group on the surface by using a plasma treatment method. It is possible to employ a method of forming a functional group on the surface by plasma treatment or the like, and a method of coating a polymer having hydrophilic and hydrophobic properties that can be controlled by light or temperature. Further, a phospholipid-polymer complex may be coated on the surface. After the above-mentioned surface treatment is carried out, a hydrophilic polymer such as polyethyleneglycol or a phospholipid-polymer complex may be immobilized.

EXAMPLES

Hereinafter, examples of the cell culture method according to the present invention will be described. However, the present invention is not limited to these examples.

Examples 1 and 2, Comparative Example 1

1. Preparation of Culture Chamber

In Examples 1 and 2 and Comparative Example 1, patterns each having the equivalent diameter D, the width W, and the height H as listed below were formed by photolithography as the culture chamber 10 in which the culture spaces 11 shown in FIGS. 1 and 2 were regularly arranged, and Ni electroplating was performed to thereby obtain molds each having a corresponding concave-convex shape.

Example 1: D=100 μm, W=20 μm, H=50 μm (H/D=0.5)
Example 2: D=200 μm, W=20 μm, H=100 μm (H/D=0.5)
Comparative Example 1: D=200 μm, W=20 μm, H=50 μm (H/D=0.25)

In Examples 1 and 2 and Comparative Example 1, the molds were used and the concave-convex pattern shape was transferred to polystyrene by hot embossing, thereby forming resin base materials having the above-mentioned dimensions. A film was prepared by forming a silicon dioxide film with a thickness of 100 nm by vacuum deposition on the surface of each resin base material, and the film was attached, by a laser welding method, to a 24-hole plate made of polystyrene and having no bottom surface. After that, γ-ray sterilization was carried out. In this manner, 24-well culture plates in which the culture chambers 10 each having the plurality of culture spaces 11 were formed in the respective wells were prepared.

In Comparative Example 2, a commercially-available, γ-ray sterilized, planar 24-well culture plate (manufactured by Becton, Dickinson and Company, Falcon/®) was used. In Comparative Example 2, cells were cultured on a flat surface, which is the conventional two-dimensional culture.

All the culture plates have a water contact angle of 45 degrees or less. The water contact angle was measured with an automatic contact angle measuring device OCA20 (manufactured by EKO Instruments Co., Ltd.). As the culture plates of Examples 1 and 2 and Comparative Example 1, flat plates with no concave-convex patterns for forming the culture spaces 11 were prepared under the same conditions, and the water contact angle was measured. In Comparative Example 2, it was definitely confirmed by visual observation that the water contact angle was 45 degrees or less.

2. Cell Culture and Observation

The culture plates used were prepared in such a manner that 300 μL of 1 vol % MPC solution was poured into the wells of all the culture plates, the culture plates were left at 4° C. for 24 hours, and then the solution was sucked by an aspirator and was completely dried.

Human HT29 colon cancer cells (DS Pharma Biomedical Co., Ltd.) were used.

The cells were allowed to proliferate to a predetermined number of cells in a 5 vol % $CO_2$ incubator at 37° C. by using a culture flask (manufactured by CORNING Incorporated). As a culture medium, a DMEM (Dulbecco's Modified Eagle Medium) (manufactured by SIGMA Corporation) culture medium containing 10 vol % fetal calf serum (FBS: Fetal Bovine Serum) was used. The cells were allowed to proliferate to a predetermined number of cells in a 5 vol % $CO_2$ incubator by using a culture flask (manufactured by CORNING Incorporated). The proliferated cells were separated from the culture bottom surface by using a 0.25 vol % trypsin solution, and the cells were collected by a centrifugal separation method. The collected cells were added to a DMEM culture medium containing 10 vol % fetal calf serum, and were seeded at a cell density of 500,000/cm². After that, the cells were cultured in a 5 vol % $CO_2$ incubator at 37° C. for 24 hours.

After the cell culture, the cells were observed with an inverted microscope.

As for the observation results, a spheroid formation rate (A), a spheroid diameter average ($D_{Av}$), and a ratio (B) of spheroids having a diameter in the range of ±5% of the average value of spheroid diameters were calculated using the following formula. The calculation results are shown in Table 1.

the spheroid formation rate $A$(%)=(the number of spheroids)×100/(the number of spaces in one visual field observed with an inverted microscope)

the spheroid diameter average $D_{Av}$(μm)=(sum of diameters of spheroids)/(total number of spheroids)

the ratio $B$(%) of spheroids having a diameter within the range of ±5% of the average value of spheroid diameters=(the number of spheroids having a diameter within the range of ±5% of the average value)×100/(total number of spheroids)

TABLE 1

| Example 1 | | | Example 2 | | | Comparative Example 1 | | | Comparative Example 2 | | |
|---|---|---|---|---|---|---|---|---|---|---|---|
| A | $D_{Av}$ | B | A | $D_{Av}$ | B | A | $D_{Av}$ | B | A | $D_{Av}$ | B |
| 79% | 41 μm | 61% | 100% | 65 μm | 73% | 33% | 73 μm | 8% | No spheroid is formed | | |

FIGS. 7 to 10 show photographs obtained by photographing the spheroids, which were cultured under the conditions of Examples and Comparative Examples, by an inverted microscope.

Example 3

1. Preparation of Culture Chamber

As the culture chamber 10 in which the culture spaces 11 shown in FIGS. 1 and 2 are regularly arranged, a pattern having the equivalent diameter D, the width W, and the height H as given below was formed by photolithography and Ni electroplating was performed, thereby obtaining a mold having a corresponding concave-convex shape.

D=200 μm, W=200 μm, H=100 μm (H/D=0.5)

In Example 3, a culture plate was prepared in the same manner as that of Examples 1 and 2 except that this mold and a 96-hole plate were used, and a 96-well culture plate was obtained.

2. Cell Culture and Observation

After the culture surface was subjected to a microwave plasma treatment and was cleaned with a phosphate buffer solution, the wells of all culture plates were coated with a 0.01 vol % MPC solution. The culture plates were left in a clean bench for 24 hours at room temperature and the MPC solution was dried.

HepG2 cells were used.

As a culture medium, a DMEM culture medium containing 10 vol % fetal calf serum was used. The culture method is similar to that of Examples 1 and 2.

Figure 11:
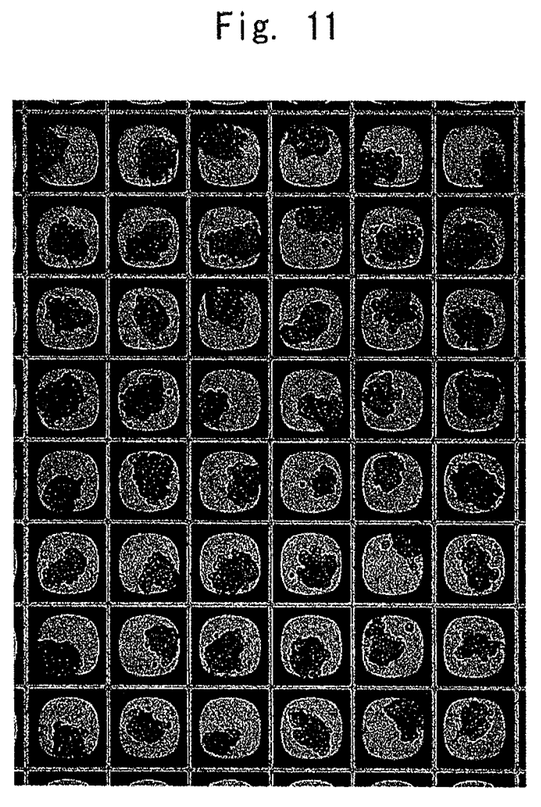
FIG. 11 is a photograph showing results of Example 3.

FIG. 11 shows the results of Example 3. As shown in the photograph of FIG. 11, formation of spheroids in the culture chamber 10 is observed also when HepG2 is cultured.

Note that the present invention is not limited to the above embodiment, but can be modified as necessary without departing from the scope of the present invention.

This application is based upon and claims the benefit of priority from Japanese patent application No. 2011-204796, filed on Sep. 20, 2011, the disclosure of which is incorporated herein in its entirety by reference.

REFERENCE SIGNS LIST

1 Culture Plate
9 Spheroid
10 Culture Chamber
11 Culture Space
12 Wall
13 Bottom Portion
21 Well
22 Partition

The invention claimed is:

1. A method of culturing adherent cells, the method comprising
   seeding adherent cells by injecting a culture medium containing the adherent cells into each culture space of a plurality of culture spaces within a culture chamber,
   culturing the adherent cells to form spheroids of the adherent cells in each culture space,
   culturing the spheroid within each culture space,
   wherein:
   each culture space has an equivalent diameter that is 1 to 3 times the diameter of a desired spheroid and said equivalent diameter is within the range of 100 μm to 200 μm;
   each culture space has a height that is 0.5 to 2 times the equivalent diameter;
   a surface of each culture space has a water contact angle of 45 degrees or less;
   each culture space has either a cylindrical shape or a rectangular prism shape, and a flat culture bottom surface;
   each culture space comprises a wall partitioning the adjacent culture spaces;
   the culture space wall has a height equal to the height of the culture space, and a thickness in the range of 5 μm to 50 μm;
   the spheroid cultured in each culture space is contained within the culture space, and does not come into contact with the spheroid in an adjacent culture space during the culturing; and
   60% or more of all cultured spheroids have a diameter within a range of 5% below to 5% above an average value of diameters of the spheroids obtained after the culturing.

2. The method of claim 1, wherein the thickness of the wall partitioning the adjacent culture spaces is in a range of 5 μm to 20 μm.

3. The method of claim 1, wherein the thickness of the wall partitioning the adjacent culture spaces is in a range of 20 μm to 50 μm.

4. The method of claim 1, wherein the wall partitioning the adjacent culture spaces has an angle formed between an upper surface and a side surface of the wall of 90 degrees.

5. The method of claim 1, wherein the spheroids are cancer cells.

6. The method of claim 1, wherein the culture chamber comprises a resin molded product comprising at least one member selected from the group consisting of an acrylic resin, a polylactic acid, a polyglycolic acid, a styrene resin, an acrylic-styrene copolymer resin, a polycarbonate resin, a polyester resin, a polyvinyl alcohol resin, an ethylene-vinylalcohol copolymer resin, a thermoplastic elastomer, a vinyl chloride resin, and a silicon resin.

7. The method of claim 1, wherein the surface of each culture space has been processed by glass processing so that the surface has a water contact angle of 45 degrees or less.

8. The method of claim 1, wherein the surface of each of the culture spaces is processed by forming a functional group thereon by plasma treatment so that the surface has a water contact angle of 45 degrees or less.

9. The method of claim 1, wherein a polymer having hydrophilic and hydrophobic properties that vary depending on temperature or light is coated on the surface of each culture space.

10. The method of claim 1, wherein a hydrophilic polymer chain that inhibits cell adhesion is immobilized on the surface of each of the culture spaces.

11. The method of claim 1, wherein a phospholipid or a phospholipid-polymer complex is immobilized on the surface of each culture space.

12. The method of claim 1, wherein the surface of each culture space has been processed by glass processing so that the surface has a water contact angle of 45 degrees or less, and thereafter a polymer having hydrophilic and hydrophobic properties that vary depending on temperature or light, a hydrophilic polymer chain that inhibits cell adhesion, a phospholipid, or a phospholipid-polymer complex is immobilized on the surface.

13. The method of claim 1, wherein the surface of each culture space has been processed by forming a functional group thereon by plasma treatment so that the surface has a water contact angle of 45 degrees or less, and thereafter a polymer having hydrophilic and hydrophobic properties that vary depending on temperature or light, a hydrophilic polymer chain that inhibits cell adhesion, one of a phospholipid, or a phospholipid-polymer complex is immobilized on the surface.

14. The method of claim 2, wherein the spheroids are cancer cells.

15. The method of claim 14, wherein:
the culture space wall partitioning the adjacent culture spaces has an angle formed between an upper surface and a side surface of the wall of 90 degrees.

16. The method of claim 1, wherein each culture space has a rectangular prism shape.

17. The method of claim 1, wherein a thickness of a bottom portion of the culture chamber is 1 mm or less.

18. A method of culturing adherent cells, the method comprising culturing a spheroid of adherent cells in each of a plurality of culture spaces within a culture chamber, wherein:

each culture space has an equivalent diameter that is 1 to 3 times the diameter of a desired spheroid;

each culture space has a height that is 0.5 to 2 times the equivalent diameter;

each culture space has walls partitioning the adjacent culture spaces, and the walls have a thickness in the range of 5 μm to 50 μm;

a surface of each culture space has a water contact angle of 45 degrees or less;

a polymer having hydrophilic and hydrophobic properties that vary depending on light is coated on the surface of each of culture space;

the thickness of a bottom portion of the culture chamber is 1 mm or less;

the spheroid in each culture space is contained within the culture space, and does not come into contact with the spheroid in an adjacent culture space during the culturing; and 60% or more of all cultured spheroids have a diameter within a range of 5% below to 5% above an average value of diameters of the spheroids obtained after the culturing.

* * * * *

UNITED STATES PATENT AND TRADEMARK OFFICE
CERTIFICATE OF CORRECTION

PATENT NO. : 10,655,107 B2
APPLICATION NO. : 14/346121
DATED : May 19, 2020
INVENTOR(S) : Yoko Ejiri et al.

Page 1 of 1

It is certified that error appears in the above-identified patent and that said Letters Patent is hereby corrected as shown below:

In the Claims

In Column 10, Lines 51-52, Claim 8, delete "each of the" and insert -- each --, therefor.

In Column 10, Line 52, Claim 8, delete "spaces is" and insert -- space has been --, therefor.

In Column 10, Line 61, Claim 10, delete "each of the" and insert -- each --, therefor.

In Column 11, Line 12, Claim 13, delete "adhesion, one of" and insert -- adhesion, --, therefor.

Signed and Sealed this
Twenty-fifth Day of August, 2020

Andrei Iancu
*Director of the United States Patent and Trademark Office*